United States Patent [19]

Howland

[11] Patent Number: 5,030,220

[45] Date of Patent: Jul. 9, 1991

[54] SPINE FIXATION SYSTEM

[75] Inventor: Robert S. Howland, Seal Beach, Calif.

[73] Assignee: Advanced Spine Fixation Systems Incorporated, Stanton, Calif.

[21] Appl. No.: 501,742

[22] Filed: Mar. 29, 1990

[51] Int. Cl.⁵ ............................. A61F 5/04; A61F 5/00
[52] U.S. Cl. ......................................... 606/61; 606/73; 128/69
[58] Field of Search ...................... 606/53, 57, 60, 61, 606/67, 69, 64, 65, 70, 72, 73, 104; 128/69; 248/67.5, 68.1

[56] References Cited

U.S. PATENT DOCUMENTS

| | | | |
|---|---|---|---|
| 476,769 | 6/1892 | Allason | 411/331 |
| 510,683 | 12/1893 | Gibson | 411/331 |
| 929,548 | 7/1909 | Brunker | 411/331 |
| 2,398,965 | 4/1946 | Rounds | 411/331 |
| 3,997,138 | 12/1976 | Crock | 606/61 |
| 4,422,451 | 12/1983 | Kalamchi | 128/69 |
| 4,448,191 | 5/1984 | Rodnyansky | 128/69 |
| 4,653,481 | 3/1987 | Howland | 128/69 |
| 4,686,970 | 8/1987 | Dove | 128/69 |
| 4,790,303 | 12/1988 | Steffe | 606/72 |
| 4,854,304 | 8/1989 | Zielke | 128/69 |
| 4,913,134 | 4/1990 | Lugue | 128/69 |

Primary Examiner—Mickey Yu
Assistant Examiner—Michael Brown
Attorney, Agent, or Firm—Beehler & Pavitt

[57] ABSTRACT

An implantable spinal fixation system includes a cancellous bone screw, such as a pedicle screw, carrying an improved saddle assembly, secured in place by a nut and which includes a simple and effective locking mechanism including a plurality of fingers which contacts each of the upper half saddle and the nut to prevent rotation of the latter relative to the remained of the assembly. The implant system also includes rods, firmly gripped by the saddle assembly and sublaminar wires in which the rod/wire interface is protected by a wire protector.

16 Claims, 6 Drawing Sheets

SPINE FIXATION SYSTEM

RELATED APPLICATION AND PATENTS

Reference is made to U.S. Pat. 4,653,481 issued on Mar. 31, 1987 and assigned to the same assignee.

FIELD OF INVENTION

This invention relates to implantable spinal fixation systems and more particularly to an improved spinal fixation system for the surgical treatment of spinal problems which may require correction, stabilization, adjustment or fixation of the spinal column or components thereof, and more particularly the lumbar and sacral portions of the spine, although the present invention is not limited thereto.

DESCRIPTION OF THE PRIOR ART

U.S. Pat. No. 4,653,481 describes the prior art and prior approaches with respect to implantable spinal fixation systems and reference is made to that disclosure which is incorporated herein by reference. Reference is also made to the prior patents disclosed in the above identified patent.

In addition to the above, there are systems known as the Syracuse system, the Luque system (Luque, Clinical Orthopaedics and Related Research, Number 203, February, 1986, Pp 126-134), the Vermont system, the Puno system, the Cotrel-Duboset system (Cotrel et al, Clinical Orthopaedics and Related Research, Number 227, February, 1988, Pp 10-23), the Harrington system (Harrington, Clinical Orthopaedics and Related Research, Number 227, February, 1988, Pp 3-5), the Edwards system, the Zielke system (Zielke et al, Clinical Orthopaedics and Related Research, Number 203, February, 1986, Pp 151-152), and the AO system. The system of the above identified patent is referred to as the WILTSE TM system. The advantages of the WILTSE system are described in the above identified patent and those advantages have led to increased use of the system with considerable success. However, as is the case with any successful spinal system, wider use thereof has led to improvement thereof. For example, the WILTSE system as described in the above patent uses both a securing nut and a locking nut to keep the upper and lower half of the saddle assembly firmly locked for good purchase on the associated rod. The result is that the length of the screw and saddle includes the length of both nuts. In some instances it is desirable to keep the profile of the portion from the bottom of the saddle to the end above the top of the saddle as short as possible to reduce muscle irritation after implant.

In other cases, the WILTSE system has been modified for use in stabilizing the lumbar spine, the latter system referred to as the SELBY TM system and which uses the basically the same screw and saddle assemblies and rods of the WILTSE system. In the SELBY system, sacral screws are inserted into the sacrum and used to anchor a saddle and clamp component. A rod is configured to fit the saddle and clamp and positioned over the vertebral process. Sublaminar stainless steel wire is then used to secure the rod in position. In this particular case, it is desired to keep the profile of the sacral screw relatively small to avoid muscle irritation in the sacral region.

Typically, stabilization of the lumbar spine is important in cases degenerative lumbar scoliosis, degenerative spondylolisthesis and spinal stenosis. These conditions commonly require decompression because of stenosis. With decompression, an already unstable spine is made more unstable and fusion is necessary. Fusion alone without some form of added internal fixation is prone to failure in many instances.

SELBY instrumentation for the posterior spine may be indicated in cases of degenerative lumbar scoliosis, degenerative spondylolisthesis and spinal stenosis, where spinal instability indicates that additional internal support is needed during the fusion process. In addition, the SELBY instrumentation may also be used in other cases, such as in reduction of spinal deformity, vertebrectomy or spinal osteotomy where support is needed.

In instances where sublaminar wires and rods are used, the wires are looped over the rods to secure the position thereof and to secure the stabilizing instrumentation to the spinal vertebrae and thus tightly contact the rod.

It is thus apparent that while the system of the above identified patent is an improvement, further improvement will only enhance the benefits of that system. These improvements involve simpler installation in less time during surgery than certain other systems, reduced muscle irritation, and more secure attachment of rods to the L5-S1 segment. Another advantage is elimination of loop migration and reduced spinal rotation. The relatively low profile also offers marked advantages.

Accordingly it is an object of this invention to provide a spinal implant system including cancellous bone screws, more particularly either pedicle or sacrum screws, or both, each carrying a support device upon which other components may be mounted and which provides a lower profile due to an improved and relatively simple locking attachment.

Another object of this invention is to provide an improved spinal implant system including cancellous bone screws, which may be sacrum or pedicle screws, or both, and which carry an improved saddle assembly for secure purchase on a rod member and wherein the profile of the saddle assembly is reduced by means of an improved and simple locking mechanism.

A further object of this invention is to provide an improved and relatively simple spinal implant system which is relatively easy to install, and which is quite effective in support and stabilization of the spine.

Still another object of this invention is to provide an improved spinal fixation system using rods and sublaminar wires in which the rod/wire interface is protected by a wire protector.

BRIEF DESCRIPTION OF THE INVENTION

The above and other objects are achieved in accordance with the present invention by an improved spinal implant system which is quite versatile and effective to stabilize and support the spine while providing implant components which are of a relatively low profile so as to reduce muscle irritation following implant.

In general, the procedure of the present invention involves the use of the mastering technique described in U.S. Pat. No. 4,653,481 and reference is made to that patent for further detailed discussion.

One aspect of this invention involves the provision of an improved locking system for use with a bone screw and saddle assembly in which the saddle assembly is effectively locked in place such that the profile of the saddle assembly and locking mechanism is markedly reduced over that of the prior art thereby reducing muscle irritation. This is achieved in accordance with this invention by a lock washer which includes an aperture and multiple fingers and which is positioned between the upper half saddle and the locking nut of either a single rod or dual rod system.

One of the fingers of the lock washer is bent downwardly and is received in an aperture provided in the upper surface of the upper half saddle. Aligned in a 180 degree orientation with the downwardly bent finger is a planar finger, while a third finger, also planar, is displaced from the planar finger. In use, the half saddles are assembled to the screw and the serrated rod, the lock washer is assemble with the bent finger in place and a polygonal nut is threaded on the threaded end of the screw. Once tightened down to secure the half saddles to the rod, the polygonal nut locks depending finger of the lock washer to the upper half saddle. The other two fingers are then bent upwardly, away from the upper half saddle, so as to contact and grip adjacent surfaces of the nut thereby preventing the latter from unscrewing. In this way, a simple and efficient and low profile locking assembly is provided for use with a single rod or dual rod system for either the WILTSE or SELBY system or other implant systems in which simple and efficient locking is desired.

Another aspect of the present invention is the provision of a wire protector for use in the SELBY system and which is received over the rod and located between the rod and the wire. The principal purpose of the wire protector is to prevent the wire or the rod from cutting into the other, especially since the rod is serrated. The wire protector may be used in any implant system in which a wire is wrapped or tied around a metal support structure.

It is apparent from the foregoing brief description that the present invention offers many advantages over the prior art spinal support and fixation systems and methodology. These and other advantages and other objects are made more easily apparent from a consideration of the several forms in which this invention may be embodied. Such forms are illustrated in the drawings accompanying and forming part of the present specification. The forms described in detail are for the purposes of illustrating the principles of the present invention; but it is to be understood that such detailed description is not to be taken in a limiting sense.

DETAILED DESCRIPTION OF THE INVENTION

Figure 1:
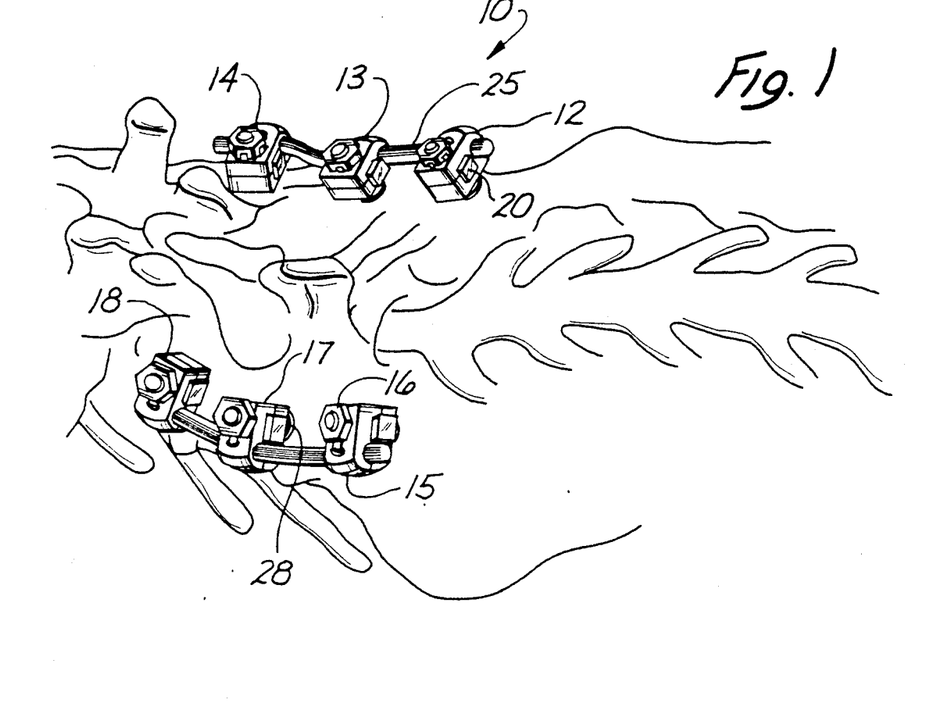
FIG. 1 is a diagrammatic view, in perspective, of two level fusion instrumentation in accordance with this invention.

Referring to the drawings, FIGS. 1 through 6 illustrate various types of uses of the improved instrumentation of this invention, although the invention is not limited to such uses as will be apparent to those skilled in the art. Thus, for example, FIG. 1 illustrates WILTSE pedicle screw instrumentation in accordance with this invention for a two level fusion from L4-L5-S1 locations.

The instrumentation 10 includes bone screw and clamp assemblies 12, 13 and 14 on one side of the spine and bone screw and clamp assemblies 16, 17 and 18 on the other side of the spine. Each of the bone screw and clamp assemblies, generically cancellous bone screws, are, in this form of essentially the same structure Each includes a threaded end portion which is screwed into the bone and a threaded end which receives a saddle assembly 20. The saddle assembly is secured in place by a locking assembly 25 to be described. The saddle assembly includes mating upper and lower half saddles which firmly grip and purchase on a rod 25. The rod is serrated as are the mating faces of the upper and lower half saddles. In this illustration, the saddle assemblies are shown assembled laterally but can be reversed and assembled with the support rod 25 medially. The illustration also shows a spacer riser 28 on the left side at the L5 location. The spacer riser allows for additional bone placement and creates a straighter support rod to simplify rod bending. The procedure for the mastering and rod bending techniques are as described in the earlier patent already identified.

Figure 2:
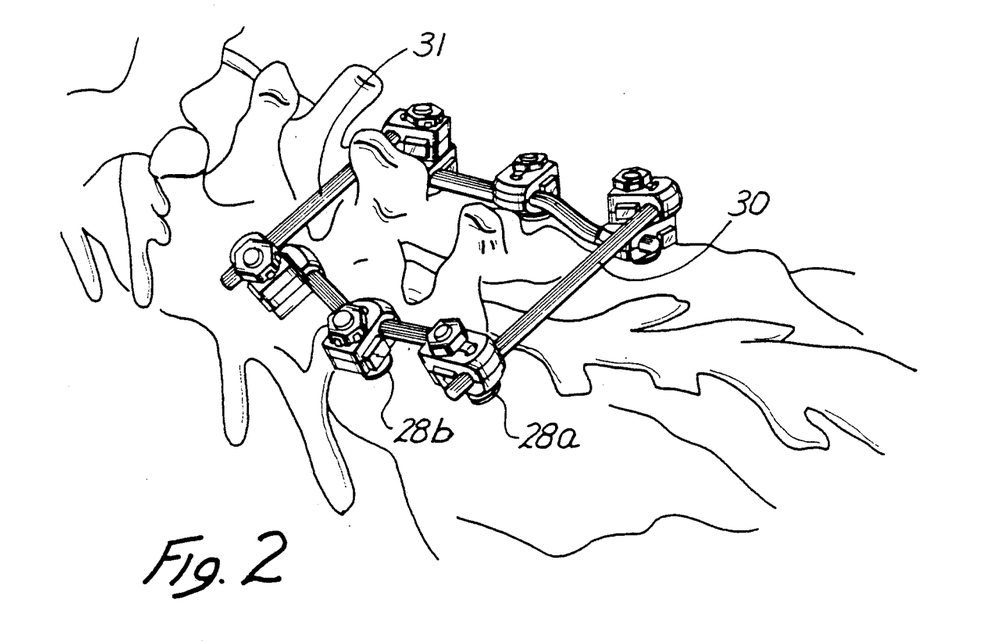
FIG. 2 is a diagrammatic view, in perspective, of two level fusion instrumentation with cross bracing in accordance with this invention.

FIG. 2 is similar to FIG. 1 but illustrates end cross bracing 30 and 31 for a two level fusion from L4-L5-S1. The saddle assemblies are shown assembled medially and various height spacer risers 28a and 28b are also shown. End bracing is typically used for severely unstable vertebrae conditions and when bone quality at the anchor screw sites is poor.

Figure 3:
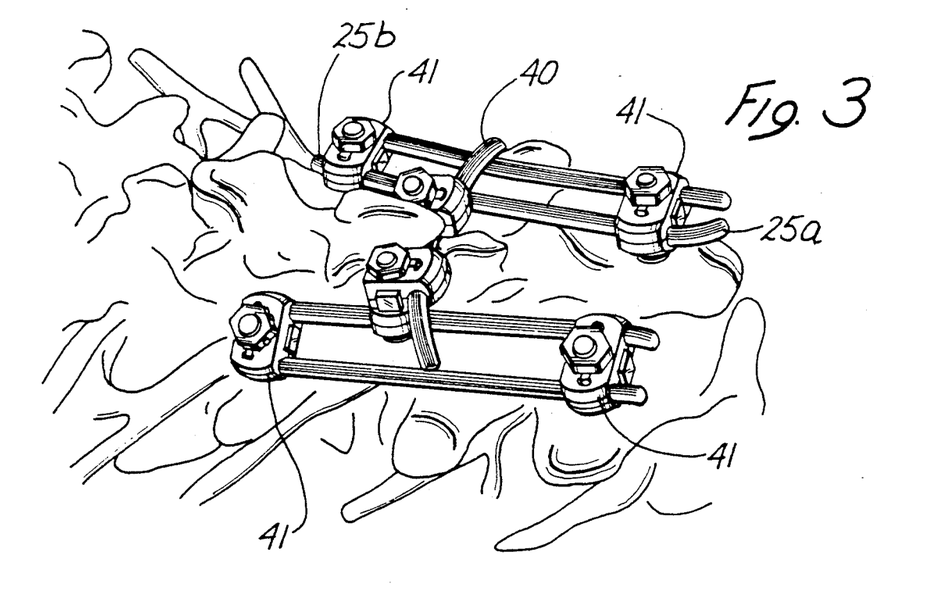
FIG. 3 is a diagrammatic view, in perspective, of two rod instrumentation with mid cross bracing in accordance with this invention.

FIG. 3 illustrates a two rod system with mid cross bracing 40 for burst fracture fusion at L2. In this form the saddle assemblies 41 can grip two rods. Mid cross bracing may also be used on one rod systems and whenever vertebrae are skipped with either one or two rod assemblies. The use of bracing adds additional strength, resistance to torsional forces and protects against screw breakage. As shown the ends 25a and 25b may be bent up or down to avoid rod dislocation from the saddle assemblies if torsional forces are high and whenever the vertebrae are set in compression.

Figure 4:
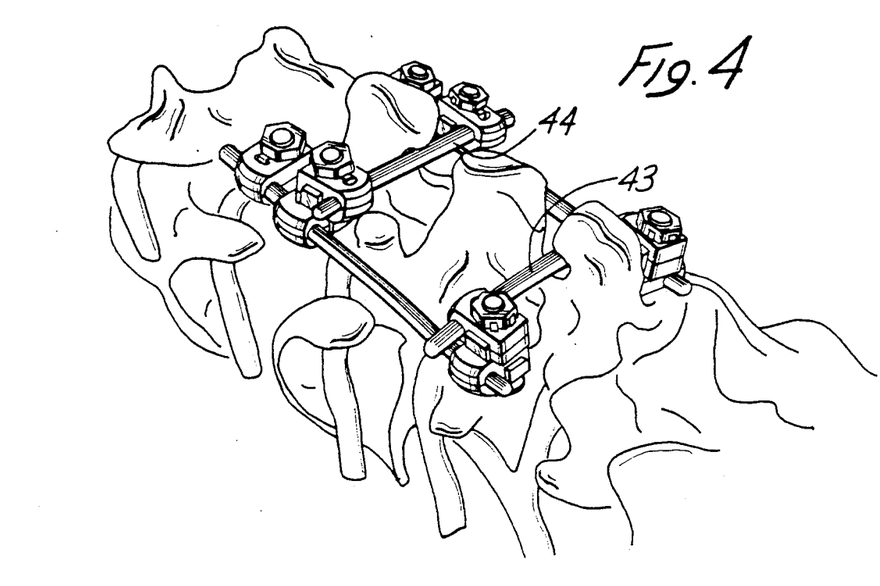
FIG. 4 is a diagrammatic view, in perspective, of one rod instrumentation with end and mid cross bracing in accordance with this invention.

FIG. 4 illustrates a single rod system in accordance with this invention with end bracing 43 and mid cross bracing 44 for a L2-L3-L4 fusion when a vertebrae is skipped. The use of end and mid cross bracing adds additional strength, resistance to torsional forces and protects against screw breakage and pull out.

Figure 5:
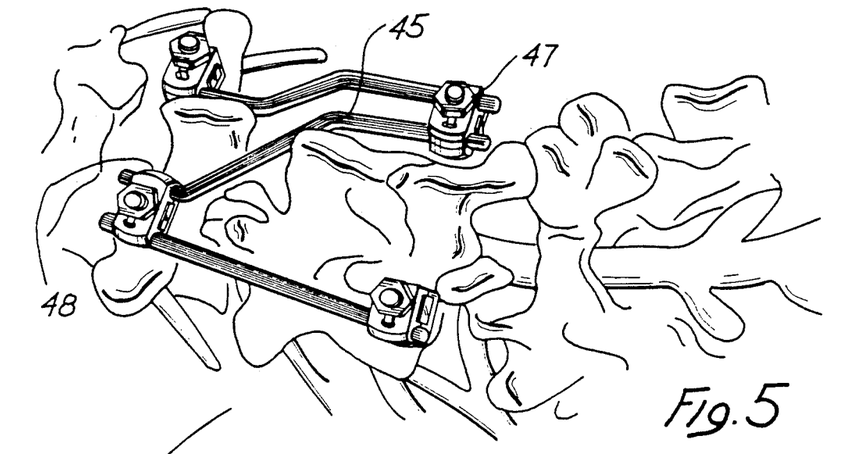
FIG. 5 is a diagrammatic view, in perspective, of cross over bracing instrumentation in accordance with this invention.

FIG. 5 illustrates a cross over bracing system in accordance with this invention in basically a one rod system for L2-L3-L4 fusion when a vertebrae is skipped. The cross over brace 45 is mounted on one of the apertures of each of the dual rod mounting assemblies 47 and 48. This assembly may also be used in a one level situation. This assembly adds additional strength, resistance to torsional forces and protects against screw breakage and pull out.

Figure 6:
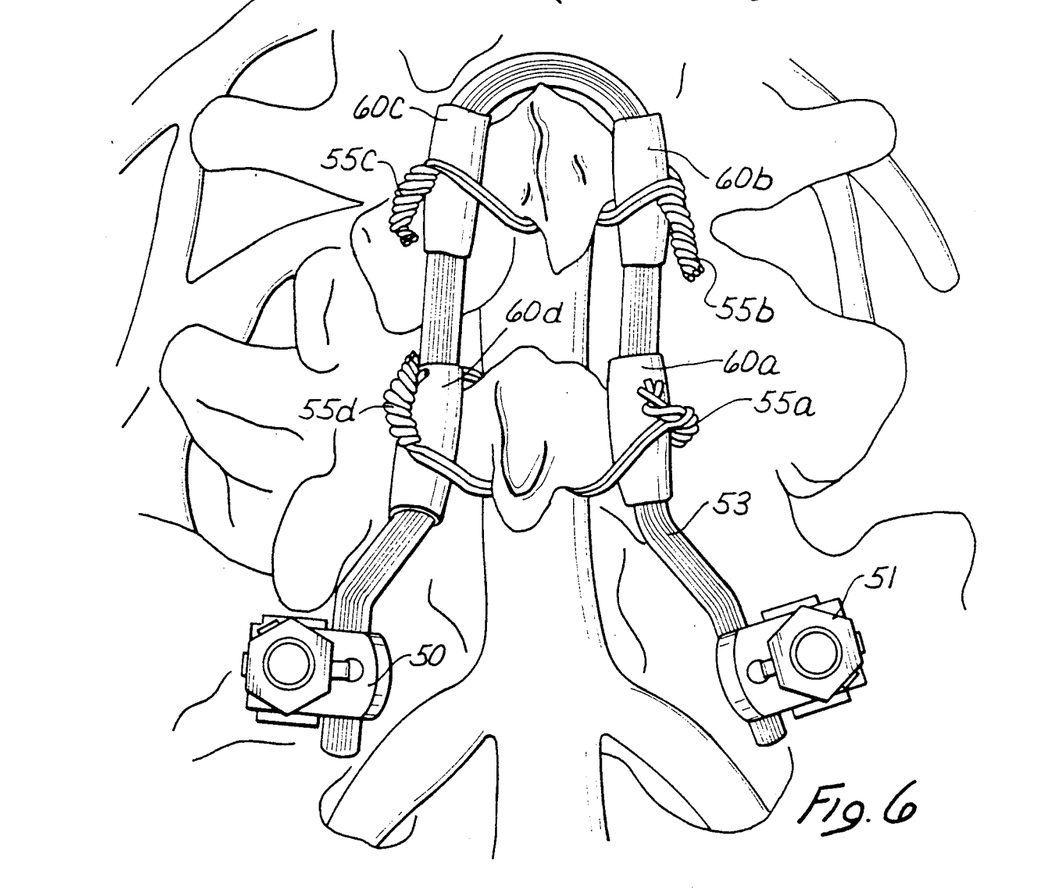
FIG. 6 is a diagrammatic view, in perspective, of sacral fusion instrumentation in accordance with this invention.

The instrumentation of FIGS. 1–5 is basically a WILTSE instrumentation with the bone screws being mounted in the pedicle while that illustrated in FIG. 6 is a SELBY instrumentation in accordance with this invention. The system includes basically sacral screw and clamp assemblies 50 and 51, a rod 53 and wiring 55a, 55b, 55c, and 55d. This instrumentation may be used, for example, in fixing L4 and L5 to S1. Sacral screws 50 and 51 are placed in the sacrum and the clamp assemblies are mounted on the threaded end by positioning the lower saddle thereon. A soft aluminum rod is placed on the lower saddle and temporarily fixed in place by a nut. Using rod bending tools, the soft aluminum master is molded along a proper course overlying the lamina of L5 and L4. The soft rod then passes around the cranial border of the spinous process of L4. The soft rod is then brought back around the opposite side, across the laminae of L4 and L5 and clamped to the opposite clamp assembly. Thus formed, the soft aluminum rod is used as a master for the serrated stainless steel rod.

The next operation is to pass the wires 55a–55d under the laminae, in approximately the positions illustrated. The serrated stainless steel rod, of a contour following that of the aluminum rod master is then placed in the respective saddle assemblies and secured in place. For maximum rigidity of the fixation system, it is important for the rod to rest firmly on the lamina and against the base of the L4 spinous process. At this point, the wire protectors 60a, 60b, 60c and 60d are placed on the rod.

The purpose of the wire protectors 60a–60d is to reduce stress on the wires during subsequent twisting and subsequent patient motion. They also operate to reduce direct contact between the wires and the serrated rod and to assume part of the compression forces during wire twisting. After the wires are twisted, the ends are cut and the wires folded as illustrated.

Figure 7:
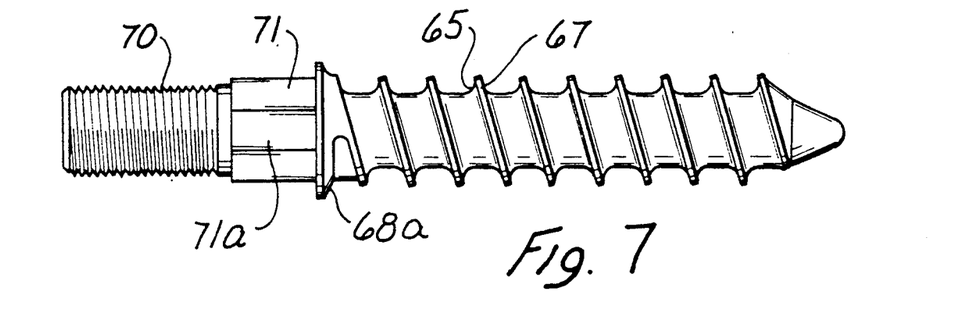
FIG. 7 is a view of an anchor screw in accordance with this invention.
Figure 7A:
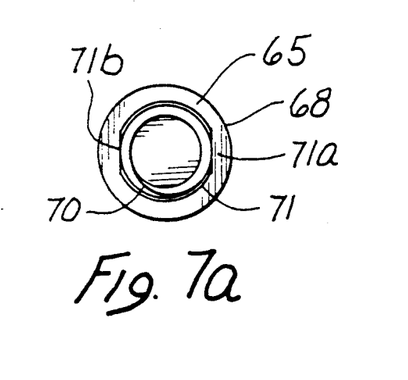
FIG. 7A is a view as seen from the left of FIG. 7.

Referring to FIGS. 7 and 7A, an anchor screw 65 in the form of a cancellous bone screw is illustrated and includes a threaded portion 67 adapted to be inserted into bone. The threaded portion terminates in a radially extending shoulder 68 which is slightly larger than the major diameter of the threaded portion 67, the underside of the shoulder being chamfered as indicated at 68a. The end 70 opposite the threaded portion is also threaded with a standard thread to receive a threaded hexagonal nut, not shown. Between the threaded end and the shoulder 68 is a generally cylindrical saddle seat section 71 whose diameter is less than the shoulder 68 but greater than the major diameter of the threaded end 70. The saddle seat section 71 includes two flats 71a and 71b located 180 degrees of each other to permit medial or lateral installation and which operate as locaters for the lower half saddle to prevent rotation of the lower half saddle relative to the screw. The screw 65, as well as the other components except for the wire, is made of 316 LVM stainless steel which is chemically polished and passivated to resist corrosion by body fluids. The screws, as will be understood, come in various lengths and diameters. While the screws carry a saddle assembly, it is understood that other support devices may be mounted on the screw and locked thereto, as will be described.

Figure 8:
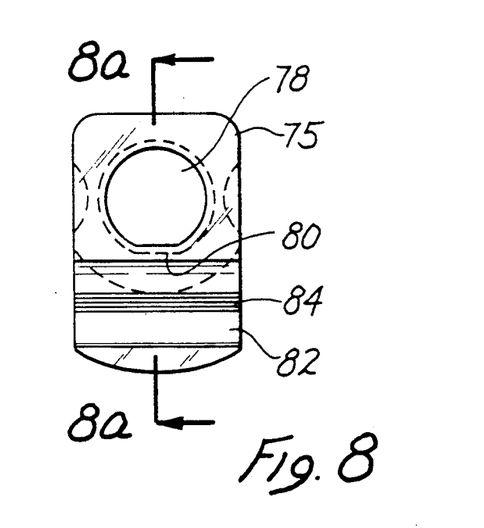
FIG. 8 is a view of the underside of a a lower saddle assembly in accordance with this invention.
Figure 8A:
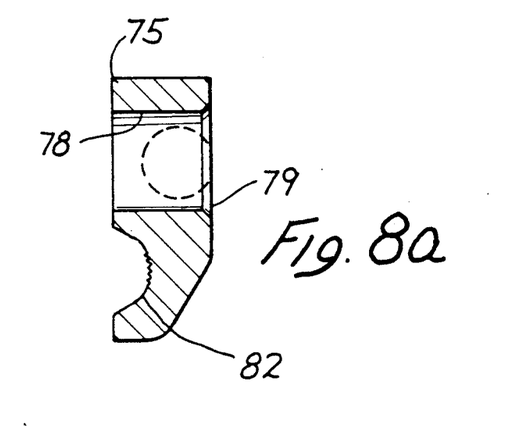
FIG. 8A is a view partly in section and partly in elevation as seen from the right of FIG. 8.

FIGS. 8 and 8A illustrate the structure of the lower half 75 of the saddle assembly and which is provided with an aperture 78 for receipt on the saddle seat section 71 of the screw 65. The lower half is assembled such that the small counterbored section 79 is seated on the shoulder 68. The surface bearing the counterbore is the lower surface while that opposite that is the upper surface. The aperture 78 is provided with a flat 80 which mates with either flat 71a or 71b for lateral or medial installation on the saddle seat section 71. The axial length of the lower half saddle is approximately that of the axial length of saddle seat section 71. The lower half of the saddle also includes an arm which forms a rod receiving half aperture 82, laterally of the aperture 78 and serrated along its length as indicated at 84 of FIG. 8 for mating gripping purchase of a serrated rod.

Figure 9:
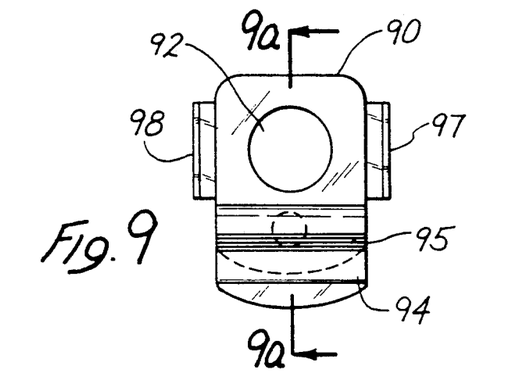
FIG. 9 is a view of the underside of an upper saddle assembly in accordance with this invention.
Figure 9A:
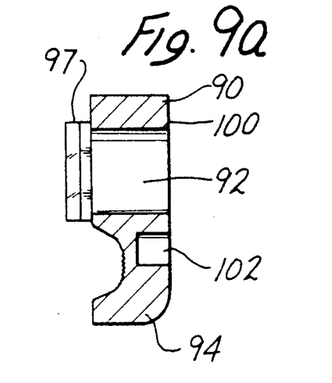
FIG. 9A is a view partly in section and partly in elevation as seen from the right of FIG. 9.
Figure 10:
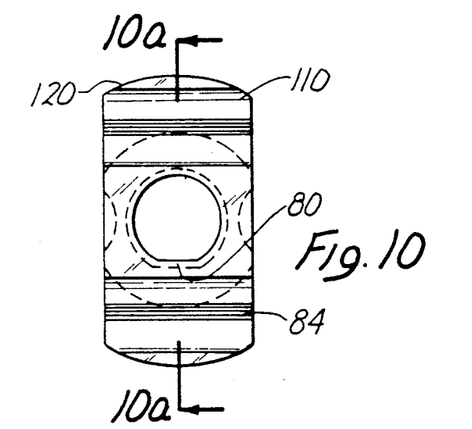
FIG. 10 is a view of the underside of a a lower saddle assembly for a two rod system in accordance with this invention.
Figure 10A:
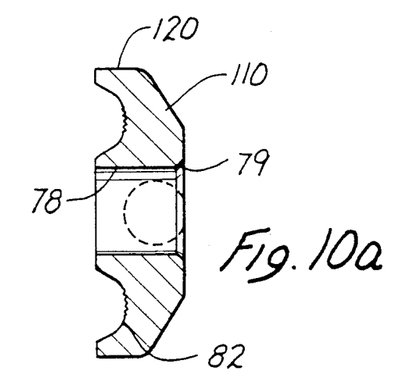
FIG. 10A is a view partly in section and partly in elevation as seen from the right of FIG. 10.
Figure 11:
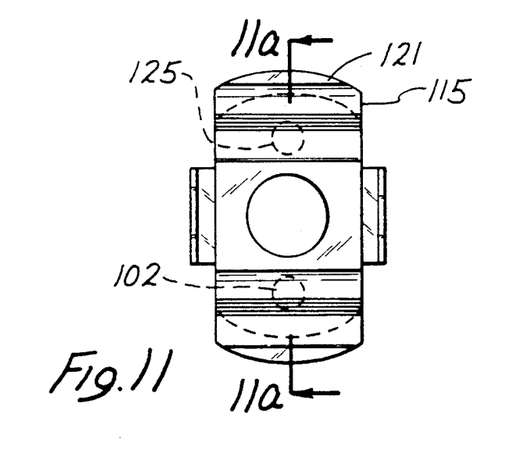
FIG. 11 is a view of the underside of an upper saddle assembly for a two rod system in accordance with this invention.
Figure 11A:
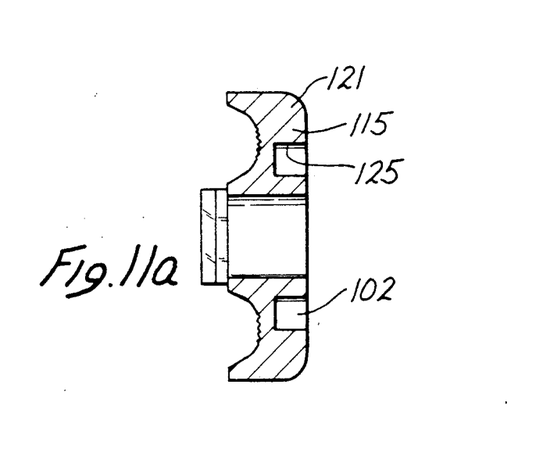
FIG. 11A is a view partly in section and partly in elevation as seen from the right of FIG. 11.

FIGS. 9 and 9A illustrate the upper half 90 of the saddle assembly of the saddle assembly and which is provided with an aperture 92 for receipt on the threaded end 70 of the screw 65. The axial length of the upper half saddle is less than that of the threaded end of the screw 65 so that when assembled, a portion of the threads is exposed. The upper half of the saddle also includes an arm forming a rod receiving half aperture 94, laterally of the aperture 98 and serrated along its length as indicated at 95 of FIG. 9 for mating gripping purchase of a serrated rod. The upper half saddle also includes spaced guide fingers 97 and 98, one on each side of the aperture 92, and dimensioned to fit over the lower half saddle and to engage the side walls thereof as the upper half is assembled on the screw with the rod receiving aperture thereof facing that of the lower half saddle. Thus assembled, the serrated surfaces are in facing relation and may tightly grip the serrated rod for firm purchase thereon upon completion of the assembly.

The upper surface 100 of the upper half saddle 90 includes an aperture 102, located laterally of aperture 92 and laterally of the fingers 97 and 98 and which forms part of a locking system, to be described.

FIGS. 10 and 10A and FIGS. 11 and 11A illustrate a lower and upper half saddle 110 and 115, respectively, for a two rod system. These half saddle assemblies are essentially the same as those previously described and thus the same reference numerals will be used for the same parts. In these structures there is a second arm 120 and 121 on each of the half assemblies and which each include a serrated half opening for gripping a second rod. The second arm 121 of the upper half saddle of the dual rod system is provided with an aperture 125 which functions essentially the same as 102.

It is understood that each of the single rod and double rod systems use a nut to secure the upper and lower half saddles in place. In the prior system, previously described in the patent referred to, a second nut was used as a lock nut with the result that the axial length of the treaded end portion 70 of the screw had to be of a dimension sufficient to accommodate two nuts, thus increasing the axial length. In some instances, this added length tended to cause muscle irritation after implant. The overall length of the screw above the upper half saddle has been reduced by the novel locking assembly of this invention.

Figure 12:
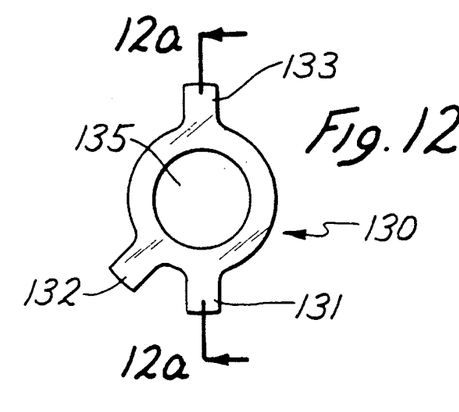
FIG. 12 is a plan view of a locking washer in accordance with this invention.
Figure 12A:
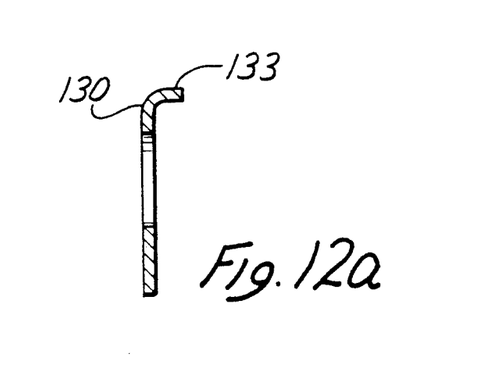
FIG. 12A is a view as seen from the right of FIG. 12.

Referring to FIGS. 12 and 12A, a unique and improved locking washer 130 is illustrated. This washer is in the form of a flat metal washer, of the metal already described and includes a plurality of fingers 131, 132 and 133 and which extend radially. The washer is provided with an aperture 135 for reception over the threaded end 70 of the screw. As seen, two of the fingers 131 and 133 are oriented 180 degrees to each other while finger 132 is offset with respect to finger 131. The offset may be 45 degrees, for example. Further, fingers 131 and 132 are planar with respect to the body of the washer, while finger 133 is bent downwardly, as seen in FIG. 12A.

In use, the screws and rod or rods are assembled over the respective lower half saddles and then the upper half saddle is installed. The lock washer 130 is then assembled over the top surface of the upper half saddle with the downwardly depending finger positioned in the aperture 102 or 125 depending on whether a single or double rod system is used. A hexagonal nut is then threaded on the threaded end portion of the screw and tightened down, being sure that the finger 133 remains in the corresponding aperture. Through the use of a suitable tool, each finger 131 and 132 is bent upwardly in a direction opposite form the orientation of finger 133, and tightly against the outer side surface of the nut. Due to the angular displacement of fingers 131 and 132, one finger will engage each of the sides of the nut forming adjacent surfaces, while the third finger is firmly anchored in the top surface of the upper half saddle and between that surface and the under surface of the nut. The result is that the nut overlies the lock washer and maintains the downwardly depending finger in place. Thus, the nut is firmly locked in place against rotation and the profile of the assembly above the upper half saddle is markedly reduced over prior locking structures. In the event that some adjustment may thereafter be necessary, the fingers 131 and 132 are bent downwardly, out of contact with the side surface of the nut and the latter is unscrewed to release the half saddles. Any required adjustment may be made and the screw and saddle assembly is then secured in place, as described, using a new lock washer.

It is apparent that nuts other than hexagonal nuts may be used with appropriate adjustment in the displacement of fingers 131 and 132 so that each bears against a different but adjacent side surface of the threaded nut. The finished assembly may be seen in FIG. 6, for example.

Figure 13:
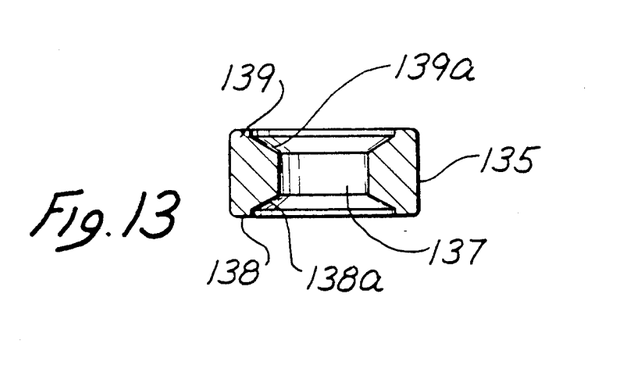
FIG. 13 is a view, partly in section and partly in elevation of a spacer in accordance with this invention.

Occasionally it is desired to raise the saddle assembly to a given plane in order to have the various clamping surfaces in planar alignment, or to have one or more elevated with respect to the remainder. FIG. 13 illustrates a spacer 135 which is received between the bottom face 68b of the screw 65 and the bone or sacrum. Such is illustrated in FIG. 2, for example. The spacer is provided with an aperture 137 for passage of the threaded portion 67 of the screw, but the latter is not screwed into the spacer. Since screws of various lengths and diameters may be used, the aperture of the spacer may vary with the particular screw. Further, since various heights may be needed, the axial length of the spacer may vary.

The principal function of the spacer, in addition to providing added height to the saddle assembly, is to provide support for the screw since not all of the threaded portion of the screw is inserted into the bone. In use, the spacer is placed over the threaded portion and the screw is then placed into the bone until the bottom face 138 contacts the bone. As illustrated each of the faces 138 and 139 are provided with a counterbore 138a and 139a to mate with the chamfer 68a of the screw thus maintaining the two in alignment. It is apparent that either 138 or 139 may be the bottom or upper face of the spacer.

Figure 14:
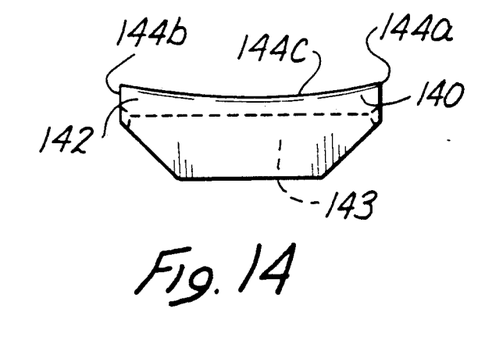
FIG. 14 is a view partly in section and partly in elevation of a wire protector in accordance with this invention.
Figure 14A:
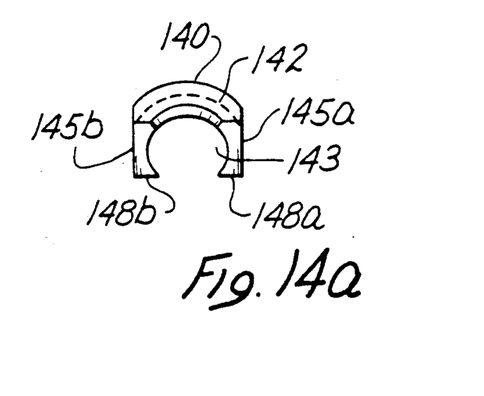
FIG. 14A is a view of the wire protector as seen from the left of FIG. 14.

As earlier noted in SELBY system, wire protectors are used for the reasons already described. Referring to FIGS. 14 and 14A the wire proctor 140 is illustrated. The wire protector is made of a suitable material such as FDA approved ultra-high molecular weight polyethylene. The wire protector includes an elongated body 142 having an aperture 143 therein, the latter being proportioned to be received on a serrated rod, as illustrated in FIG. 6. As shown, the diameter of the wire protector is greater at the ends 144a and 144b than in the middle 144c such that the outer upper surface is dished. In this way, the wire is held centered with respect to the axial length of the wire protector. The wire protector also includes flat side walls 145 and 145b, the latter forming resilient side walls which terminate at ends 148a and 148b which are over center of the mid-point in order to grip the rod firmly. As seen in FIG. 14, the side walls are recessed back such that the axial dimension of the bottom end of the side walls is less than the axial dimension measured between 144a and 144b. In this way, it is easier to assemble the wire protector on the rod. Further, the straight side walls tend to reduce interference with any adjacent bone structure.

It is apparent from the foregoing detailed description that the present invention has many advantages over the support systems and methods of the prior art, as heretofore set forth. It will be apparent that various modifications may be made to the support fixation and methodology of this invention by those skilled in the art without departing from the scope of the appended claims.

What is claimed is:

1. A cancellous bone screw and clamp assembly for use in a spinal support system for support and fixation of at least portions of the spinal column comprising:

a screw clamp shaft member having a threaded end portion adapted to be screwed into a preselected location of the spinal column or sacrum and a threaded end opposite the threaded end portion,     a saddle assembly mounted on the threaded end of said shaft member and including mating upper and lower half saddles which form at least one pair of spaced rod receiving apertures,     said apertures being in spaced relation and each including serrated opposed faces to receive a rod serrated along its length to effect purchase securely on the rod assembled thereto and to prevent rotation of the rod relative to said saddle assembly, nut means received on the threaded end of said shaft assembly to secure the mating half saddles together such that the serrated rod positioned in the rod receiving apertures are gripped by the mating half saddles along a predetermined length of the serrated surface of said rod to secure said rod firmly to said screw clamp assembly in a predetermined orientation with respect to the spinal column or sacrum, lock means to prevent said nut means from unthreading, and said lock means being located between said nut means and said upper half saddle and including a plurality of spaced finger means some of which engage said nut means and others of which engage said upper half saddle to prevent rotation of said nut means relative to the threaded end of said shaft assembly.

2. A cancellous bone screw and clamp assembly as set forth in claim 1 wherein said lock means includes a plurality of fingers, one of said fingers being displaced downwardly and the others initially being in a planar orientation, means in the upper half saddle for receiving said downwardly displaced finger, and said other fingers being displaced in a direction opposite of said downwardly displaced finger to engage said nut means along a surface portion thereof to prevent rotation of said nut means relative to said screw clamp shaft member.

3. A cancellous bone screw and clamp assembly as set forth in claim 1 wherein said saddle assembly receives a single serrated rod.

4. A cancellous bone screw and clamp assembly as set forth in claim 1 wherein said saddle assembly receives dual serrated rods.

5. A cancellous bone screw and clamp assembly as set forth in claim 1 wherein a serrated single rod is received in said saddle assembly, wire means securing said rod to said spinal column, and wire protector means between said wire and said serrated rod.

6. A cancellous bone screw and clamp assembly as set forth in claim 5 wherein said wire protector means includes a dished surface between said wire and said serrated rod means.

7. In a cancellous bone screw and locking assembly including a bone screw member having a threaded portion for insertion into a bone and a threaded end portion carrying support means to be fixedly attached to said bone screw by a nut threaded on the threaded end of said bone screw, an improved locking system comprising:

locking means received on the threaded end of said bone screw member between said nut and said support means, said locking means including a plurality of spaced fingers, means in said support means for receiving one of the fingers of said locking means, and the other of said locking means contacting said nut to prevent rotation thereof relative to said bone screw member.

8. A cancellous bone screw and locking assembly as set forth in claim 7 wherein said one finger extends in one direction and the other of said fingers extend in another direction.

9. A cancellous bone screw and locking assembly as set forth in claim 7 wherein said support means includes an upper surface, said means for receiving one of said fingers including means in said upper surface, and said other of said fingers being disposed in an orientation opposite from said upper surface.

10. A cancellous bone screw and locking assembly as set forth in claim 7 wherein said locking means includes three spaced fingers angularly oriented, two of said fingers being oriented in 180 degree relation and one being initially planar and the other being bent in a first direction, the third finger being initially planar and displaced relative to said planar finger, and said second and third fingers being displaced in a direction opposite that of said first finger.

11. A cancellous bone screw and locking assembly as set forth in claim 7 further including rod means carried by said support means, wire means securing said wire means to a bone member, and wire protector means positioned between said rod means and said wire means.

12. A spinal support and fixation system for internal fixation of the posterior spine comprising:

bone screw and clamp assemblies adapted to be mounted at selected portions of the spine, rod means having portions adapted to be received in said clamp assemblies, nut means for securing said clamp assemblies to said bone screw, locking means for locking said nut means to said clamp assemblies and including a plurality of fingers, said locking means being located between said nut means and said clamping assemblies, means in said clamp assemblies for receiving one of the fingers of said locking means, and the other of said locking means contacting said nut to prevent rotation thereof relative to said bone screw member.

13. A spinal support and fixation system for internal fixation of the posterior spine comprising:

bone screw and clamp assemblies adapted to be mounted at selected portions of the spine, rod means having portions adapted to be received in said clamp assemblies of said bone screw and clamp assembly, said rod means including a portion which passes around the cranial border of the spinous process, sublaminar wiring for securing said rod means to said spine, and wire protector means carried by said rod means and positioned between said rod means and said sublaminar wiring.

14. A spinal support and fixation system as set forth in claim 13 wherein said wire protector means includes a surface portion in contact with said sublaminar wiring, said surface portion being dished, said wire protector means including spaced flat side walls, and said wire protector having means forming and aperture for reception on said rod means.

15. A spinal support and fixation system as set forth in claim 13 wherein said wire protector includes a body and an upper surface in contact with said sublaminar wiring, the cross section of said body and upper surface is greater at the ends thereof than at the mid-section thereof.

16. A spinal support and fixation system as set forth in claim 15 wherein said body includes an aperture for reception of rod means, said body including spaced side walls having outer flat surfaces, and the axial dimension of said upper surface portion being greater than the axial dimension of said side walls.

* * * * *